United States Patent [19]

Neuman et al.

[11] Patent Number: 5,079,535
[45] Date of Patent: Jan. 7, 1992

[54] STRAIN GAUGE AND METHOD OF MAKING AND USING THE SAME

[75] Inventors: Michael R. Neuman, Chesterland, Ohio; Timothy G. McIntyre, Melbourne Beach, Fla.

[73] Assignee: Case Western Reserve University, Cleveland, Ohio

[21] Appl. No.: 580,653

[22] Filed: Sep. 11, 1990

[51] Int. Cl.⁵ ............................................. G01L 1/22
[52] U.S. Cl. ........................................ 338/2; 338/5; 338/6; 338/283; 73/862.65; 73/775
[58] Field of Search .................. 338/2, 3, 4, 5, 6, 283; 73/862.64, 862.65, 775

[56] References Cited

U.S. PATENT DOCUMENTS

| | | | |
|---|---|---|---|
| 4,038,867 | 8/1977 | Andrews et al. | 338/6 X |
| 4,646,563 | 3/1987 | Jones | 338/4 X |
| 4,658,233 | 4/1987 | Uchida et al. | 338/5 |

Primary Examiner—Marvin M. Lateef
Attorney, Agent, or Firm—John W. Logan, Jr.

[57] ABSTRACT

A strain gauge primarily designed for dynamic measurements and requiring very little force to produce a change in length. The strain gauge is alternately concave and convex in shape, such as a sinusoidal curve with nodes of low resistance on the convex portions and strain gauges of high resistance on the concave portions. The gauge is unbonded and can be stretched with very little force. The strain gauge is utilized in an instrument to monitor infant respiration and detect episodes of apnea.

10 Claims, 2 Drawing Sheets

STRAIN GAUGE AND METHOD OF MAKING AND USING THE SAME

BACKGROUND OF THE INVENTION

1. Field of the Invention

This invention relates to a strain gauge having alternate sections of concave and convex, concave and flat or square wave shapes that can be stretched with very little force and to a method of making such a strain gauge.

2. Description of the Prior Art

Heretofore, most strain gauges were of the type adapted to be bonded to a substrate to provide a measurement of strain of an object. In the measurement of dynamic movement, such as abdominal movement of an infant to monitor respiration, such a strain gauge would be unsatisfactory in that it would restrict movement and interfere with the breathing process. One strain gauge which has been used for this purpose in the past, is the mercury strain gauge. This comprises a flexible thin wall rubber tube filled with a conductive medium such as mercury and having electrical contacts at opposite ends. As the tube is stretched, the body of mercury becomes longer and thinner and the resistance through the gauge is increased. This type of gauge, in this application, has several drawbacks. First, as oxygen diffuses through the rubber tube, the mercury can oxidize and provide intermittent electrical contact. Also, because of the toxic nature of mercury, use of the gauge is limited to a carefully watched clinical setting and can not be used at home. Other home use infant respiratory monitors are subject to false readings and at times can be unreliable.

SUMMARY OF THE INVENTION

The strain gauge of the present invention includes an elongated base of polyester or similar material which may be easily flexed and has alternating concave and convex sections, such as corrugations, extending widthwise of the base. Strain gauge sections of high resistance are provided on the concave sections of the base subject to tension when the base is elongated while low resistance connections or nodes are provided on the convex sections.

A principal object of the present invention is to provide a novel strain gauge which has very little resistance to stretching, does not have to be bonded to a substrate for its full length and which will not interfere with or restrict movement of the object being tested or monitored.

Another object of the present invention is to provide a novel strain gauge designed to detect dynamic movement of a body rather than measure strain and not interfere with such dynamic movement.

Yet another object of the present invention is to provide a strain gauge that will convert large elongations into small surface strains within the range of the strain gauge.

A further object of the present invention is to provide a novel infant respiration and apnea sensor which can be taped or otherwise secured at its opposite ends to an infant's abdomen or thorax and detect movement due to breathing without impairing the infant's breathing effort and also detect episodes of apnea.

Still another object of the present invention is to provide novel apparatus for monitoring respiration in infants which is reliable, non-toxic and suitable for both home and hospital use.

DETAILED DESCRIPTION OF THE INVENTION

Figure 1:
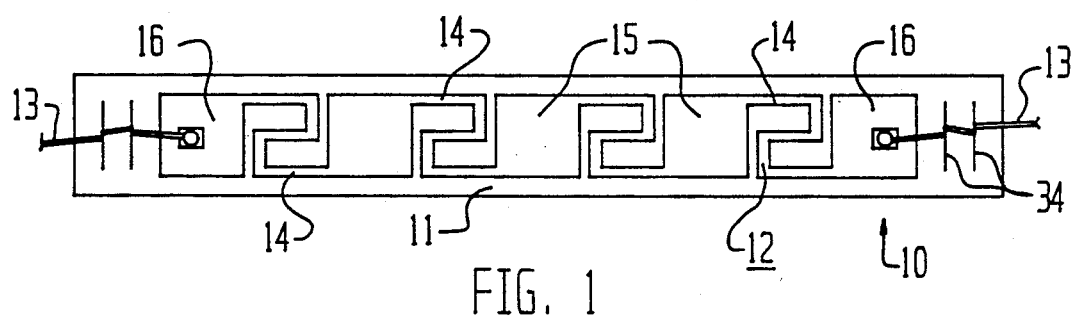
FIG. 1 is a top plan view of a strain gauge made in accordance with the present invention.
Figure 2:
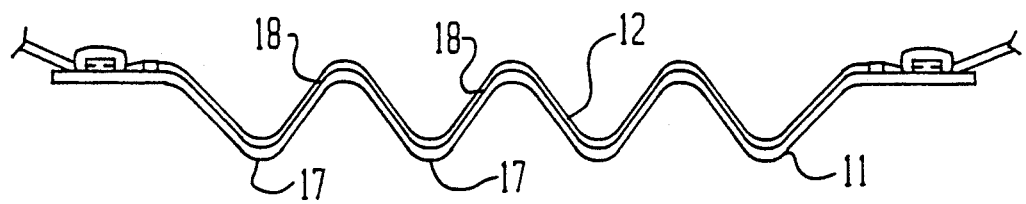
FIG. 2 is a side elevational view of the strain gauge of FIG. 1.

Referring more specifically to the drawings and particularly FIGS. 1 and 2, there is illustrated one form of strain gauge 10 which comprises a base 11 having a strain gauge resistor pattern 12 formed on the upper surface of the base with electrical connectors 13, 13 at opposite ends thereof. As shown in FIG. 1, the base is of elongated rectangular shape and the strain gauge resistor pattern extends longitudinally thereof.

The base is formed of a non-conductive material that can be flexed repeatedly. In the application of the strain gauge of the present invention to monitor infant respiration and detect episodes of apnea, a polyester film has been found to be extremely satisfactory. One film tested successfully is polyethylene terephthalate, commercially available as Mylar film, a product of E. P. DuPont DeNemours Company. Type D Mylar film has the smoothest surface available in this material and can readily receive the resistor film by metalizing. Again, for this above application, a polyester film thickness of 127 micrometers was found to have the desired flexibility. Thinner films would not withstand the heat of metallization and thicker films, while suitable for other applications, provided too great a resistance to movement in monitoring infant respiration.

To manufacture the present strain gauge, the strain gauge resistor pattern is preferably formed on the upper surface of the base by a conventional vacuum evaporation method. This method includes cleaning and heat stabilizing the Mylar base, placing the bases in a vacuum chamber along with the desired coating material, heating the substrate or base and drawing the necessary vacuum. The metal vaporizes and is deposited in a film of uniform thickness on the substrate to be coated. The resistor film can be of any suitable conductive material or combination of materials well known in the art for this use. One requirement however is that the selected material be sufficiently ductile or elastic to withstand repeated flexing without cracking.

One such material that has been found suitable for this strain gauge is gold. It is ductile, it can be evaporated at relatively low temperatures, it can be patterned and etched by well known established processes and lead wires can be attached by soldering.

Other materials that can be used with the vacuum evaporation process include palladium and aluminum. With gold and palladium, a thin layer of chromium should first be deposited on the base to increase film adhesion. Other well known metallic alloys can also be used for the resistor and applied to the base by sputtering or by chemical vapor deposition.

After the resistor material is applied to the base, the desired patterning can be accomplished by etching or otherwise well known processes. For the etching process, the conventional photolithographic process can be used, exposing a coating of photosensitive material applied to the resistor material through a mask, developing it and rinsing away or otherwise removing the unexposed portions. Thereafter, the unprotected areas of the resistor coating are removed by etching in suitable acid solutions.

One suitable pattern of resistor material is shown in FIG. 1. Here, the resistor coating includes a series of spaced apart strain gauge resistor segments 14 interconnected by larger unetched nodes 15 of much lower resistance than the strain gauge segments. Unetched nodes 16 are also provided at the terminal ends to provide for attachment of the lead wires 13.

An important feature of the present invention resides in shaping the strain gauge, after completion of the strain gauge resistor pattern so that it may be readily extended, return to its original condition upon release of the stretching force and will show a marked increase in resistance when extended. To this end, the base 11, after completion of processing of the strain gauge resistor pattern, is corrugated widthwise to provide alternating concave and non-concave sections when viewed from the top surface containing the strain gauge resistor pattern. These corrugated sections extend widthwise of the base and the strain gauge resistor pattern is such that the strain gauge resistor segments reside on the concave sections while the nodes or segments of low resistance reside on the non-concave sections.

The reason for placing the strain gauge resistor segments on the concave sections and nodes of low resistance on the convex sections of the corrugated base is that as the substrate is stretched and flattens somewhat, the surface of the concave sections experience tension. This causes a stretching of the strain gauge resistor segment on that surface thus increasing its resistance. Similarly, the convex surface experiences compression which would decrease resistance of a strain gauge resistor segment on that section. However, with a large node of low resistance on that surface under compression, its slight decrease in resistance has little effect on the overall resistance increase during stretching.

Figure 2A:
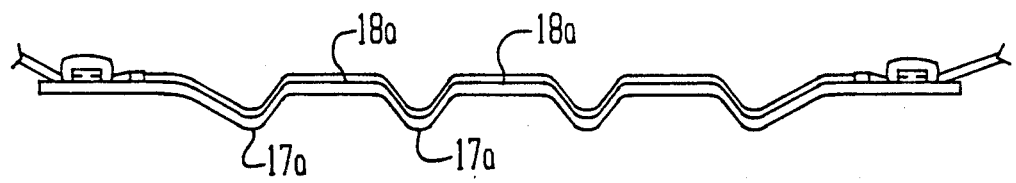
FIG. 2a is a side elevational view of a modified strain gauge of FIG. 1.

Preferably, the base is corrugated as shown in FIG. 2 having alternating concave and convex segments 17 and 18 respectively. This configuration provides for the least resistance to elongation. An alternate form of corrugation is shown in FIG. 2a in which there are concave sections 19 separated by generally flat sections 20. In this form, the strain gauge resistor pattern is as in FIG. 2, with the resistor segments 14 on the concave sections 19 and the nodes 15 on the flat sections 20. A further modified form could be a square or modified square wave shape.

If the base is formed of Mylar, the corrugating is preferably carried out by thermoforming. This can be accomplished by heating the Mylar base for a short period of time, shaping it in a forming fixture or mold and thereafter immediately quenching the base and fixture in water. One suitable heating cycle is 140° C. for twenty minutes, followed by shaping and quenching in cold water. During the shaping or molding operation, it is advisable to protect the resistor material from abrasion by the application of a coating or a strip of tape such as Teflon tape.

Figure 3:
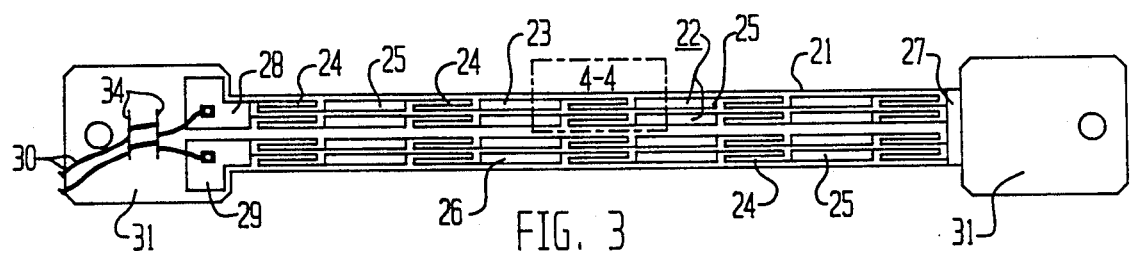
FIG. 3 is a top plan view of a modified form of strain gauge of the present invention prior to corrugating.
Figure 4:
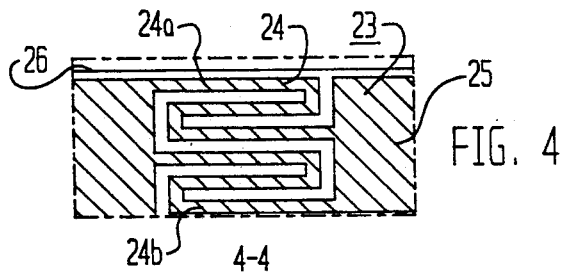
FIG. 4 is an enlarged view of a portion of FIG. 3 showing the resistor pattern.
Figure 5:
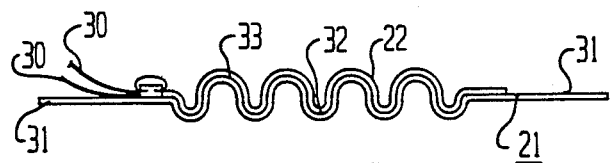
FIG. 5 is a side elevational view of the finished strain gauge of FIG. 3.

A modified strain gauge pattern is shown in FIGS. 3 and 4. This strain gauge includes a base 21 of the same material as the base 11 on which the strain gauge resistor pattern 22 is formed. The strain gauge resistor pattern, segments of which are shown in FIG. 4, includes a first leg 23 formed of a continuing series of strain gauge resistor segments 24 interconnected by larger unetched nodes 25. The resistor segments 24 comprise two parallel resistor elements 24a and 24b each of serpentine shape, as more clearly shown in FIG. 4, extending between adjacent nodes 25. This provides two separate resistor elements in parallel between each node, permitting the gauge to continue to function should one resistor element be broken. The resistor pattern further includes a second leg 26 also containing a duplicate of the pattern of resistor segments 24 and nodes 25. These two legs 23 and 26 are electrically connected at one end by the unetched conductive segment 27 and terminate at their opposite ends in separate conductive terminals 28 and 29. Lead wires 30 are adapted to be soldered or otherwise connected to the terminals 28 and 29. The base 21 can terminate at its ends in enlarged pad portions 31, 31 providing a means for attachment to an object to be monitored. After the strain gauge resistor pattern is applied to the base, the base is corrugated, for example, as shown in FIG. 5 with the resistor segments on the concave portions 32 and the nodes on the convex portions 33.

In order to limit strain on the connections for the wires, two small cuts 34 may be made in the substrate extending perpendicular to the axis of the base. The lead wires may be looped about the resulting strip of the base material, as shown in FIGS. 1 and 3, transferring any tension on the lead wires from the solder connection to the substrate.

As set forth previously, one particular application for which this strain gauge has been designed is monitoring infant respiration to detect incidents of apnea. To accomplish this, the strain gauge sensor is placed across an infant's abdomen in a direction circumferential of the body and the opposite ends of the sensor and taped to the infant by surgical tape. Preferably, the sensor is slightly stretched before being taped in place. As the infant inhales, the strain gauge is stretched, increasing its resistance and as the infant exhales, the strain gauge is relaxed. The change in resistance is measured by a conventional balanced wheatstone bridge circuit, amplified, and the output may be recorded on a suitable recorder and used to activate an audible alarm. The change in amplitude of the output signal is proportional to the infants individual breath amplitude. Thus, the generated respiration wave form provides a true picture of the infant's breathing pattern.

While particular embodiments of the present invention have been illustrates and described herein, it is not intended to limit the invention to such a disclosure and changes and modifications may be incorporated therein within the scope of the following claims.

What is claimed is:

1. A strain gauge comprising an elongated flexible base portion of generally uniform thickness, said base portion having lengthwise and widthwise dimensions, said widthwise dimension being smaller than said lengthwise dimension, said base portion having at least one intermediate concave section extending widthwise thereof and said base portion having two terminal end sections, said end sections being movable towards and away from each other;

a strain gauge resistor bonded to said base portion within said concave section and adapted to change its resistance value as said terminal end sections move in relation to each other and cause said concave section to be flexed;

and means electrically connecting said resistor to at least one of said terminal end sections.

2. A strain gauge in accordance with claim 1 in which said base includes a plurality of spaced-apart concave sections separated by intermediate sections;

a strain gauge resistor segment bonded within each said concave sections;

and means electrically connecting adjacent strain gauge resistor segments across said intermediate sections.

3. A strain gauge in accordance with claim 2 wherein said strain gauge resistor segments and electrical connecting means are formed from a continuous film of conductive material.

4. A strain gauge in accordance with claim 2 wherein said flexible base contains a plurality of corrugations extending widthwise thereof in its midportion and terminates in flat end sections, said corrugations provided said base with alternating concave and convex sections when viewed from the top surface thereof;

and said strain gauge resistor segments and electrical connecting means being bonded to said top surface.

5. A strain gauge in accordance with claim 4 wherein said strain gauge resistor segments and said electrical connecting means are formed from a continuous strip of conductive material deposited on said one surface, said strain gauge resistor segments formed of narrow strips of said conductive material and said electric connecting means formed of solid areas of said conductive material.

6. A strain gauge in accordance with claim 5 wherein said strain gauge resistor segments have one end thereof connected to one of said electrical connecting means and the other end thereof connected to the next adjacent electrically connecting means.

7. A strain gauge in accordance with claim 6 wherein a pair of said strain gauge resistor segments extend in parallel between adjacent electrical connecting means.

8. A strain gauge in accordance with claim 3 wherein a pair of parallel strips of conductive material extend lengthwise of said base, said strips being electrically connected at one end of said base, said strips of conductive material having similar patterns of alternating strain gauge resistor segments and electrical connecting means formed therefrom.

9. A strain gauge in accordance with claim 8 including electric lead wires, said lead wires being connected to the ends of said strips opposite of those connected to said end of said base.

10. A strain gauge in accordance with claim 8 wherein said strain gauge resistor segments each include two similar resistors extending parallel to one another.

* * * * *